(12) United States Patent
Koma

(10) Patent No.: US 10,189,754 B2
(45) Date of Patent: Jan. 29, 2019

(54) BUTADIENE PRODUCTION SYSTEM AND BUTADIENE PRODUCTION METHOD

(71) Applicant: SEKISUI CHEMICAL CO., LTD., Osaka (JP)

(72) Inventor: Satoshi Koma, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/527,033

(22) PCT Filed: Jan. 13, 2016

(86) PCT No.: PCT/JP2016/050844
§ 371 (c)(1),
(2) Date: May 16, 2017

(87) PCT Pub. No.: WO2016/114306
PCT Pub. Date: Jul. 21, 2016

(65) Prior Publication Data
US 2017/0327435 A1   Nov. 16, 2017

(30) Foreign Application Priority Data
Jan. 13, 2015   (JP) .................. 2015-004460

(51) Int. Cl.
*C07C 1/20* (2006.01)
*B01J 23/20* (2006.01)
(Continued)

(52) U.S. Cl.
CPC ............... *C07C 1/20* (2013.01); *B01J 23/20* (2013.01); *B01J 23/46* (2013.01); *B01J 23/464* (2013.01);
(Continued)

(58) Field of Classification Search
CPC . B01J 23/20; B01J 23/464; B01J 21/08; B01J 23/58; B01J 23/6562; B01J 23/80;
(Continued)

(56) References Cited

U.S. PATENT DOCUMENTS

2014/0058146 A1   2/2014   Bricker et al.

FOREIGN PATENT DOCUMENTS

| CN | 1724151 | 1/2006 |
| CN | 102424359 | 5/2013 |

(Continued)

OTHER PUBLICATIONS

International Search Report dated Mar. 15, 2016 in International (PCT) Application No. PCT/JP2016/050844.
(Continued)

*Primary Examiner* — Sharon Pregler
(74) *Attorney, Agent, or Firm* — Wenderoth, Lind & Ponack, L.L.P.

(57) ABSTRACT

A butadiene production system and a butadiene production method are provided in which butadiene can be produced with a high yield. The butadiene production system (1) includes: a gas preparation device (10) that heats raw materials to prepare a mixed gas including hydrogen and carbon monoxide; an ethanol production device (12) that is provided downstream of the gas preparation device (10) and brings the mixed gas including hydrogen and carbon monoxide into contact with a first catalyst to obtain ethanol; a butadiene production device (16) that is provided downstream of the ethanol production device (12) and brings the ethanol into contact with a second catalyst to obtain butadiene; and return means (18) for returning hydrogen, which is produced as a by-product in the butadiene production device (16), to the ethanol production device (12). In addi-
(Continued)

tion, in the butadiene production method, the butadiene production system (1) is used.

10 Claims, 2 Drawing Sheets

(51) Int. Cl.
*B01J 23/46* (2006.01)
*C01B 3/38* (2006.01)
*C07B 61/00* (2006.01)
*C07C 11/167* (2006.01)
*C10K 3/00* (2006.01)
*C01B 3/34* (2006.01)
*C07C 29/151* (2006.01)
*C10J 3/82* (2006.01)
*C10K 3/06* (2006.01)

(52) U.S. Cl.
CPC ............... *C01B 3/34* (2013.01); *C01B 3/38* (2013.01); *C07B 61/00* (2013.01); *C07C 11/167* (2013.01); *C07C 29/1518* (2013.01); *C10J 3/82* (2013.01); *C10K 3/00* (2013.01); *C10K 3/06* (2013.01); *C01B 2203/0216* (2013.01); *C01B 2203/06* (2013.01); *C10J 2300/0946* (2013.01); *Y02P 20/52* (2015.11)

(58) Field of Classification Search
CPC ............... B01J 23/8926; B01J 23/8993; B01J 37/0207; C01B 2203/0216; C01B 2203/06; C01B 3/34; C07C 1/20; C07C 29/1518; C07C 31/08; C10G 11/18; C10G 2300/1011; C10G 2300/708; C10G 9/36
See application file for complete search history.

(56) References Cited

FOREIGN PATENT DOCUMENTS

| | | |
|---|---|---|
| JP | 09-221437 | 8/1997 |
| JP | 2012-001441 | 1/2012 |
| JP | 2012-217886 | 11/2012 |
| JP | 2013-121939 | 6/2013 |
| JP | 2013-199461 | 10/2013 |
| WO | 2007/117590 | 10/2007 |
| WO | 2010/092819 | 8/2010 |
| WO | 2012/054798 | 4/2012 |
| WO | 2012/058508 | 5/2012 |
| WO | 2012/087949 | 6/2012 |
| WO | 2013/081779 | 6/2013 |
| WO | 2013/125389 | 8/2013 |
| WO | 2014/049158 | 4/2014 |

OTHER PUBLICATIONS

Extended European Search Report dated Jun. 1, 2018 in European Patent Application No. 16737377.8.

BUTADIENE PRODUCTION SYSTEM AND BUTADIENE PRODUCTION METHOD

TECHNICAL FIELD

The present invention relates to a butadiene production system and a butadiene production method.

Priority is claimed on Japanese Patent Application No. 2015-4460, filed on Jan. 13, 2015, the content of which is incorporated herein by reference.

BACKGROUND ART

Butadiene such as 1,3-butadiene is used as a raw material of styrene-butadiene rubber (SBR) or the like. In general, butadiene is purified from a C4 fraction which is produced as a by-product when ethylene is synthesized from petroleum.

However, recently, bioethanol synthesized from a biomass-derived raw material has attracted attention as an alternative raw material to petroleum. For example, PTL 1 discloses a method of producing butadiene from ethanol using a catalyst.

However, in the method of obtaining butadiene from ethanol using the catalyst as in PTL 1, the yield is not industrially sufficiently high.

CITATION LIST

Patent Literature

[PTL 1] PCT International Publication No. WO2013/125389

SUMMARY OF INVENTION

Technical Problem

An object of the present invention is to provide a butadiene production system and a butadiene production method in which butadiene can be produced with a high yield.

Solution to Problem

A butadiene production system (apparatus) according to an embodiment of the present invention includes: a gas preparation device that heats raw materials to prepare a mixed gas including hydrogen and carbon monoxide; an ethanol production device that is provided downstream of the gas preparation device and brings the mixed gas including hydrogen and carbon monoxide into contact with a first catalyst to obtain ethanol; a butadiene production device that is provided downstream of the ethanol production device and brings the ethanol into contact with a second catalyst to obtain butadiene; and return means for returning hydrogen, which is produced as a by-product in the butadiene production device, to the ethanol production device.

A butadiene production system (apparatus) according to another embodiment of the present invention includes: a gas preparation device that heats raw materials to prepare a mixed gas including hydrogen and carbon dioxide; an ethanol production device that is provided downstream of the gas preparation device and brings the mixed gas including hydrogen and carbon dioxide into contact with a third catalyst to obtain ethanol; a butadiene production device that is provided downstream of the ethanol production device and brings the ethanol into contact with a second catalyst to obtain butadiene; and return means for returning hydrogen, which is produced as a by-product in the butadiene production device, to the ethanol production device.

It is preferable that the return means include a pipe through which the butadiene production device and the ethanol production device are connected.

A butadiene production method according to an embodiment of the present invention includes: a gas preparation step of heating raw materials to prepare a mixed gas including hydrogen and carbon monoxide; an ethanol production step of bringing the mixed gas into contact with a first catalyst to obtain ethanol; a butadiene production step of bringing the ethanol into contact with a second catalyst to obtain butadiene; and a return step of returning hydrogen, which is produced as a by-product in the butadiene production step, to the ethanol production step.

A butadiene production method according to another embodiment of the present invention includes: a gas preparation step of heating raw materials to prepare a mixed gas including hydrogen and carbon dioxide; an ethanol production step of bringing the mixed gas into contact with a third catalyst to obtain ethanol; a butadiene production step of bringing the ethanol into contact with a second catalyst to obtain butadiene; and a return step of returning hydrogen, which is produced as a by-product in the butadiene production step, to the ethanol production step.

Advantageous Effects of Invention

In the butadiene production system according to the present invention, butadiene can be produced with a high yield.

In the butadiene production method according to the present invention, butadiene can be produced with a high yield.

DESCRIPTION OF EMBODIMENTS

The definitions of the following terms are applied to this specification and claims.

The meaning of "returning hydrogen to the ethanol production device" includes a configuration of returning hydrogen to a portion, which is provided upstream of the ethanol production device, where hydrogen returned due to an equilibrium reaction represented by $CO_2+H_2 \Leftrightarrow CO+H_2O$ is not consumed. For example, a configuration is included in which, in the pipe through which the gas preparation device and the ethanol production device are connected, hydrogen is returned to a portion where the temperature of the mixed gas is a temperature (for example, 200° C. to 800° C.) which is lower than a temperature (for example, 1000° C. to 1200° C.) at which the equilibrium reaction is shifted to the carbon monoxide side.

The meaning of "returning hydrogen to the ethanol production step" includes a step of returning hydrogen to a step before the ethanol production step where the temperature of the mixed gas is lower than a temperature at which the equilibrium reaction is shifted to the carbon monoxide side (for example, a step where the temperature of the mixed gas is 200° C. to 800° C.).

"Raw materials" are organic materials from which the mixed gas including hydrogen and carbon monoxide is obtained by heating, and include both of solid raw materials such as biomass or organic waste and raw material gases such as natural gas or waste gas.

"The ratio $H_2/CO$ between hydrogen and carbon monoxide supplied to the ethanol production step" refers to a ratio between hydrogen and carbon monoxide in a state where the mixed gas supplied from the gas preparation step to the ethanol production step is brought into contact with hydrogen returned to the ethanol production step by the return step. The same shall be applied to "the ratio $H_2/CO_2$ between hydrogen and carbon monoxide supplied to the ethanol production step".

"CO conversion ratio" refers to a percentage of the number of moles of carbon monoxide consumed by a reaction to the number of moles of carbon monoxide in the mixed gas.

"Selection ratio" refers to a percentage of the number of moles of carbon monoxide converted into a specific compound to the number of moles of carbon monoxide consumed in the mixed gas.

First Embodiment (Butadiene Production System)

In a butadiene production system according to the present invention, raw materials are heated to prepare a mixed gas including hydrogen and carbon monoxide, ethanol is obtained from the mixed gas, and butadiene is produced from the ethanol. Hereinafter, an example of the butadiene production system according to the present invention will be described.

Figure 1:
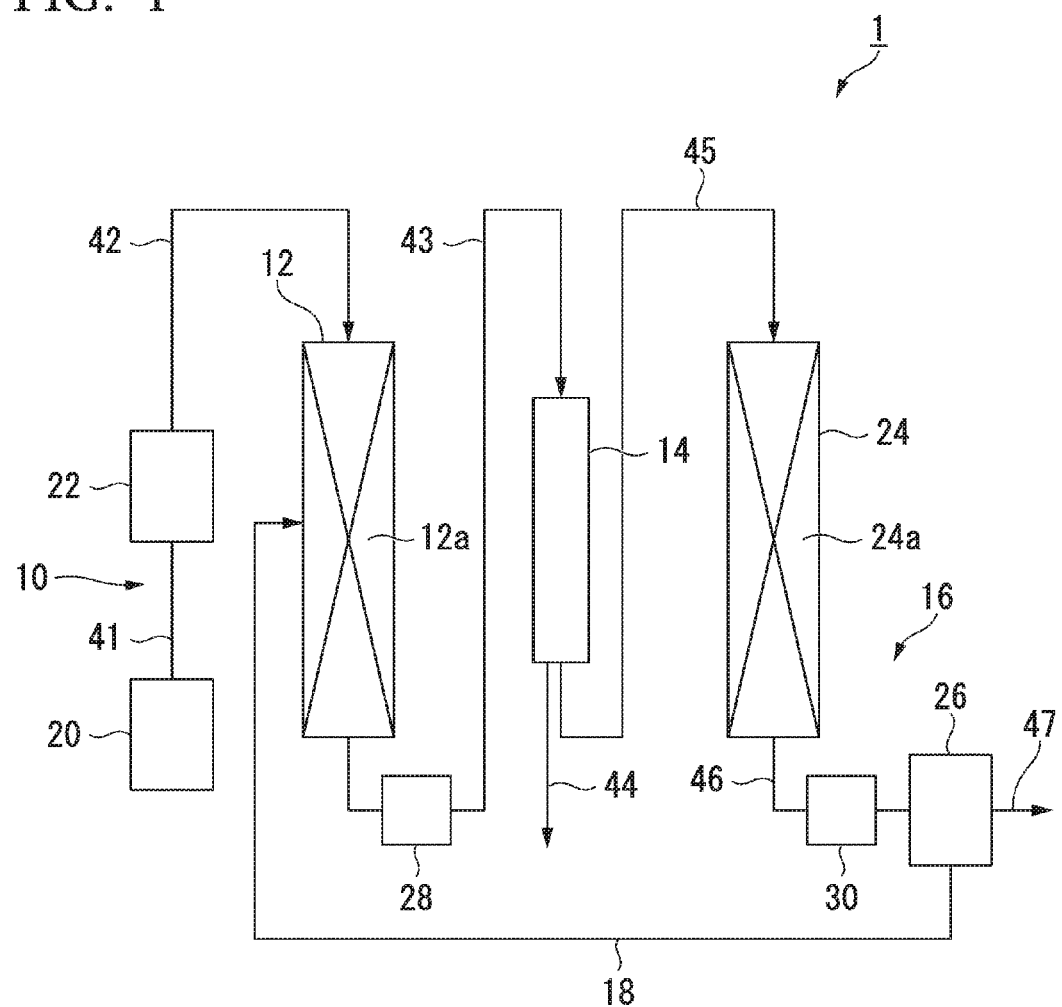
FIG. 1 is a schematic diagram showing an example of a butadiene production system according to the present invention.

As shown in FIG. 1, a butadiene production system 1 according to the embodiment includes: a gas preparation device 10; an ethanol production device 12 that is provided downstream of the gas preparation device 10; a purification device 14 that is provided downstream of the ethanol production device 12; a butadiene production device 16 that is provided downstream of the purification device 14; and return means 18 for returning hydrogen from the butadiene production device 16 to the ethanol production device 12. The gas preparation device 10 includes a gasification furnace 20 and a reforming furnace 22 that is provided downstream of the gasification furnace 20. The butadiene production device 16 includes a reaction pipe 24 and a gas-liquid separator 26 that is provided downstream of the reaction pipe 24.

The gasification furnace 20 and the reforming furnace 22 are connected to each other through a pipe 41. The reforming furnace 22 and the ethanol production device 12 are connected to each other through a pipe 42. The ethanol production device 12 and the purification device 14 are connected to each other through a pipe 43. An exhaust pipe 44 is connected to the purification device 14. The purification device 14 and the reaction pipe 24 of the butadiene production device 16 are connected to each other through a pipe 45. The reaction pipe 24 and the gas-liquid separator 26 are connected to each other through a pipe 46. A pipe 47 is connected to the gas-liquid separator 26.

In this example, the ethanol production device 12 and the gas-liquid separator 26 of the butadiene production device 16 are connected to each other through a pipe included in the return means 18.

The gas preparation device 10 heats raw materials to prepare a mixed gas including hydrogen and carbon monoxide at an arbitrary ratio, and includes the gasification furnace 20 and the reforming furnace 22.

The gasification furnace 20 thermally decomposes solid raw materials such as biomass, organic waste (for example, waste plastic, waste paper, or waste cloth), or coal to produce a mixed gas including hydrogen and carbon monoxide. As the gasification furnace 20, for example, a furnace that can produce the mixed gas by firing a portion of biomass or organic waste in the presence of oxygen so as to be thermally oxidized can be adopted. As the gasification furnace, a fluidized bed type gasification furnace is preferable. The fluidized bed type gasification furnace is preferable from the viewpoint that it is not likely to be affected by the forms of the raw materials and the viewpoint that the amount of auxiliary fuel used is small.

The reforming furnace 22 hydrocarbon in the mixed gas reacts with water so as be reformed into hydrogen and carbon monoxide. In the reforming furnace 22, the concentration of carbon monoxide in the mixed gas produced from the gasification furnace 20 is increased such that a ratio between hydrogen and carbon monoxide is adjusted to a desired value. For example, a ratio $H_2/CO$ of hydrogen to carbon monoxide in the reforming furnace 22 is adjusted to 1/2 to 4/1.

As the reforming furnace 22, for example, a cylindrical member which can heat the mixed gas in the presence of water vapor at a temperature higher than a temperature for the thermal decomposition in the gasification furnace 20 can be adopted.

It is preferable that the pipe 41 be formed of a material which is inert with the mixed gas and, for example, be formed of a stainless steel pipe.

In the gas preparation device 10, the solid raw materials are thermally decomposed in the gasification furnace 20 to produce the mixed gas including hydrogen and carbon monoxide, and hydrocarbon in the mixed gas reacts with water in the reforming furnace 22 to be reformed into a mixed gas having a higher carbon monoxide concentration.

As in the case of the pipe 41, it is preferable that the pipe 42 be formed of a material which is inert with the mixed gas and, for example, be formed of a stainless steel pipe.

It is preferable that a gas purifier be provided in the pipe 42. By providing the gas purifier in the pipe 42, impurities in the mixed gas such as tar, sulfur, nitrogen, chlorine, or water can be removed.

As the gas purifier, for example, various well-known gas purifiers of the related art using a wet method, a dry method, or the like can be adopted. Examples of the wet method include a sodium hydroxide method, an ammonia absorption method, a lime-plaster method, and a magnesium hydroxide method. Examples of the dry method include an absorption method such as pressure swing absorption (PSA) and an electron beam method.

In the pipe 42, a cooler for reducing the temperature of the mixed gas may be provided. By providing the cooler in the pipe 42, it is easy to sufficiently reduce the temperature of the mixed gas supplied to the ethanol production device 12. In addition, by rapidly cooling the mixed gas using the cooler, the shift of equilibrium may be prevented, and the concentration of carbon monoxide can be maintained at a high level.

The ethanol production device 12 is filled with a first catalyst to form a reactor bed 12a.

It is preferable that the ethanol production device 12 be formed of a material which is inert with the mixed gas and ethanol. In addition, it is preferable that the ethanol production device 12 have a shape that can endure heating at about 100° C. to 500° C. or pressing at about 10 MPa. As the ethanol production device 12, for example, a substantially circular stainless steel member is used.

The reactor bed 12a may be any one of a fixed bed, a moving bed, a fluidized bed, and the like.

The mixed gas is supplied to the ethanol production device 12 without any change from the gas state.

The first catalyst is a catalyst for synthesizing ethanol from hydrogen and carbon monoxide. As the first catalyst, a well-known catalyst can be adopted, and a metal catalyst is preferable. Examples of a catalyst metal used in the metal catalyst include a hydrogenation-active metal and an aggregate of a hydrogenation-active metal and an auxiliary active metal described below.

In a case where ethanol is synthesized from a mixed gas of hydrogen and carbon monoxide using the metal catalyst, typically, a primary product including acetaldehyde or acetic acid is obtained in addition to ethanol due to the following reactions (1) to (5).

$$2H_2+2CO \rightarrow CH_3COOH \quad (1)$$

$$3H_2+2CO \rightarrow CH_3CHO+H_2O \quad (2)$$

$$2H_2+CH_3COOH \rightarrow C_2H_5OH+H_2O \quad (3)$$

$$H_2+CH_3CHO \rightarrow C_2H_5OH \quad (4)$$

$$4H_2+2CO \rightarrow C_2H_5OH+H_2O \quad (5)$$

As the hydrogenation-active metal, a well-known metal of the related art in which ethanol can be synthesized from the mixed gas can be adopted. Examples of the hydrogenation-active metal include: alkali metals such as lithium and sodium; elements belonging to Group 7 in the periodic table, such as manganese and rhenium; elements belonging to Group 8 in the periodic table, such as ruthenium; elements belonging to Group 9 in the periodic table, such as cobalt and rhodium; and elements belonging to Group 10 in the periodic table, such as nickel and palladium.

Among these, hydrogenation-active metals, one kind may be used alone, and two or more kinds may be used in combination. As the hydrogenation-active metal, from the viewpoints of further improving the CO conversion ratio and improving the selection ratio of ethanol, a combination of rhodium, manganese, and lithium, a combination of ruthenium, rhenium, and sodium, or a combination of rhodium or ruthenium, an alkali metal, and another hydrogenation-active metal is preferable.

Examples of the auxiliary active metal include titanium, magnesium, and vanadium. By not only the hydrogenation-active metal but also the auxiliary active metal being supported on the metal catalyst, the CO conversion ratio and the selection ratio of ethanol and acetaldehyde can be further improved.

As the metal catalyst, a rhodium catalyst having a composition represented by the following Formula (m1) is preferable.

$$aRh \cdot bMn \cdot cMe^1 \cdot dMe^2 \quad (m1)$$

In Formula (m1), $Me^1$ represents an alkali metal, $Me^2$ represents an auxiliary active metal, and a, b, c, and d represent molar fractions in which a+b+c+d=1.

From the viewpoint of easily increasing the CO conversion ratio, a in Formula (m1) preferably represents 0.053 to 0.98, more preferably 0.24 to 0.8, and still more preferably 0.32 to 0.67.

From the viewpoint of easily increasing the CO conversion ratio, b in Formula (m1) preferably represents 0.0006 to 0.67, more preferably 0.033 to 0.57, and still more preferably 0.089 to 0.44.

From the viewpoint of easily increasing the CO conversion ratio, c in Formula (m1) preferably represents 0.00056 to 0.51, more preferably 0.026 to 0.42, and still more preferably 0.075 to 0.33.

d may be 0 (that is, the auxiliary active metal is not included) and may be more than 0 (that is, the auxiliary active metal is included). In a case where the auxiliary active metal is included, from the viewpoint of increasing the CO conversion ratio, d preferably represents 0.0026 to 0.94, more preferably 0.02 to 0.48, and still more preferably 0.039 to 0.25.

As the metal catalyst, a rhodium catalyst may be used in combination with another metal catalyst other than a rhodium catalyst. Examples of the other metal catalyst include a catalyst in which copper alone or copper and another transition metal other than copper are supported on a support (hereinafter, also referred to as "copper catalyst"). It is preferable that the copper catalyst be represented by the following Formula (m2).

$$eCu \cdot fMe^3 \quad (m2)$$

In Formula (m2), $Me^3$ represents a transition metal other than copper, and e and f represent molar fractions in which e+f=1.

As $Me^3$ in Formula (m2), zinc or chromium is preferable. As $Me^3$, one transition metal may be used alone, or two or more transition metals may be used in combination.

From the viewpoint of increasing the yield of ethanol, e preferably represents 0.5 to 0.9 and more preferably 0.5 to 0.7.

From the viewpoint of increasing the yield of ethanol, f preferably represents 0.1 to 0.5 and more preferably 0.3 to 0.5.

In a case where a rhodium catalyst and a copper catalyst are used in combination as the metal catalyst, it is preferable that the rhodium catalyst do not include copper and the copper catalyst do not include rhodium.

As the metal catalyst, a so-called supported catalyst in which a catalyst metal is supported on a porous support is preferable. In the case of the supported catalyst, a ratio between ethanol and acetaldehyde in a product can be easily controlled.

A material of the porous support is not particularly limited, and examples thereof include silica, zirconia, titania, and magnesia. Among these, silica is preferable because various products thereof having different specific surface areas and different pore diameters are commercially available.

The size of the porous support is not particularly limited. For example, in the case of a silica porous support, the particle size thereof is preferably 0.5 to 5000 μm. The particle size of the porous support is adjusted by sieving. Further, it is preferable that the particle size distribution of the porous support be as narrow as possible.

The sum of pore volumes (total pore volume) in the porous support is not particularly limited and is preferably 0.01 to 1.0 mL/g and more preferably 0.1 to 0.8 mL/g. In a case where the total pore volume is the lower limit value or higher, the specific surface area of the porous support is sufficiently large, the support amount of the metal catalyst is sufficient, and thus a decrease in the CO conversion ratio is easily prevented. In a case where the total pore volume is the upper limit value or lower, the diffusion rate of the mixed gas is not excessively fast, and the contact time between the catalyst and the mixed gas is sufficient. Therefore, a decrease in the selection ratio of ethanol is easily prevented.

The total pore volume is a value measured using a water titration method. In the water titration method, water molecules are adsorbed on a surface of the porous support, and a pore distribution is measured based on aggregation of the molecules.

The average pore diameter of the porous support is not particularly limited and is preferably 0.1 to 8 nm and more preferably 3 to 6 nm. In a case where the average pore diameter is the lower limit value or higher, the support amount of the metal catalyst is sufficient, and thus a decrease in the CO conversion ratio is easily prevented. In a case where the average pore diameter is the upper limit value or lower, the diffusion rate of the mixed gas is not excessively fast, and the contact time between the catalyst and the mixed gas is sufficient. Therefore, a decrease in the selection ratio of ethanol is easily prevented.

The average pore diameter is a value measured using the following method. In a case where the average pore diameter is 0.1 nm or more and less than 10 nm, the average pore diameter is calculated based on the total pore volume and a BET specific surface area. In a case where the average pore diameter is 10 nm or more, the average pore diameter is measured using a porosimeter according to a mercury press-in method.

Here, the total pore volume is a value measured using a water titration method, and the BET specific surface area is a value calculated based on the adsorbed amount measured by using nitrogen as an adsorption gas and the pressure in the measurement.

In the mercury press-in method, mercury is pressed in the pores of the porous support, and the average pore diameter is calculated based on the pressure at this time and the amount of mercury pressed in.

The specific surface area of the porous support is not particularly limited and is preferably 1 to 1000 m$^2$/g and more preferably 10 to 800 m$^2$/g. In a case where the specific surface area is the lower limit value or more, the support amount of the catalyst metal is sufficient, and the CO conversion ratio is further increased. In a case where the specific surface area is the upper limit value or lower, the diffusion rate of the mixed gas is more appropriate, and the selection ratio of ethanol is further increased.

The specific surface area is a BET specific surface area measured using a BET gas adsorption method in which nitrogen is used as an adsorption gas.

The product of the total pore volume and the specific surface area in the porous support is preferably 1 to 1000 mL·m$^2$/g$^2$ and more preferably 100 to 500 mL·m$^2$/g$^2$. In a case where the product is the lower limit value or more, the support amount of the catalyst metal is sufficient, and the CO conversion ratio is further increased. In a case where the product is the upper limit value or lower, the diffusion rate of the mixed gas is more appropriate, and the selection ratio of ethanol is further increased.

The state where the hydrogenation-active metal or the auxiliary active metal is supported on the metal catalyst is not particularly limited and, for example, may be a state where the metal in the form of a powder is supported on the porous support, or may be a state where the metal in the form of a metal element is supported on the porous support. Among these, the state where the metal in the form of a metal element is supported on the porous support is preferable. In the state where the metal in the form of a metal element is supported on the porous support, the contact area between the metal catalyst and the mixed gas is increased, and the CO conversion ratio and the selection ratio of ethanol are further increased.

The support amount of the catalyst metal on the porous support is determined in consideration of the kind and composition of the catalyst metal, the material of the porous support, and the like and is preferably 0.05 to 30 parts by mass and more preferably 1 to 10 parts by mass with respect to 100 parts by mass of the porous support. In a case where the support amount is the lower limit value or more, the support amount of the metal is sufficient, and the CO conversion ratio and the selection ratio of ethanol are easily improved. In a case where the support amount is the upper limit value or lower, the amount of the auxiliary active metal is not excessively large, hydrogenation-active metal is likely to be uniformly and highly dispersed, and thus the CO conversion ratio and the selection ratio of ethanol are easily increased.

The supported catalyst can be produced using a well-known method of producing a supported catalyst of the related art. Examples of the method include an impregnation method and an ion exchange method. Among these, an impregnation method is preferable. In a case where the metal catalyst is produced using an impregnation method, a metal is more uniformly dispersed, and the contact efficiency between the metal catalyst and the mixed gas is further improved. Therefore, the CO conversion ratio and the selection ratio of ethanol can be further improved.

In the embodiment, the pipe 43 includes a pressure control portion 28. The pressure control portion 28 is not particularly limited as long as it can adjust the internal pressure of the ethanol production device 12 to an arbitrary value. For example, a well-known pressure valve is used.

The purification device 14 removes materials (for example, acetic acid, ethyl acetate, unreacted mixed gas, a culture medium, or a catalyst) other than ethanol and acetaldehyde from the primary product.

Examples of the purification device 14 include a device including a separation membrane. Examples of the separation membrane include an acidic gas-containing gas treatment separation membrane described in PCT International Publication No. WO2014/080670 and a porous support-zeolite membrane composite described in PCT International Publication No. WO2013/125661.

The materials removed by the purification device 14 are exhausted through the exhaust pipe 44. It is preferable that the exhaust pipe 44 be formed of a material which is inert with the materials removed by the purification device 14 and, for example, be formed of a stainless steel pipe.

It is preferable that the pipe 45 be formed of a material which is inert with ethanol and acetaldehyde and, for example, be formed of a stainless steel pipe.

The butadiene production device 16 brings ethanol into contact with a second catalyst to obtain butadiene. The butadiene production device 16 includes: the reaction pipe 24 in which ethanol is brought into contact with a second catalyst to obtain butadiene; and the gas-liquid separator 26 that separates butadiene from a secondary product including butadiene obtained in the reaction pipe 24. The butadiene production device 16 may further include a well-known device, for example, a gas flow rate control portion that regulates the flow rate such as mass flow rate of gas.

The reaction pipe 24 is filled with the second catalyst to form a reactor bed 24a. It is preferable that the reaction pipe 24 be formed of a material which is inert with ethanol. In addition, it is preferable that the reaction pipe 24 have a shape that can endure heating at about 100° C. to 500° C. or pressing at about 10 MPa. As the reaction pipe 24, for example, a substantially circular stainless steel member is used.

The reactor bed 24a may be any one of a fixed bed, a moving bed, a fluidized bed, and the like.

The second catalyst is not particularly limited as long as butadiene can be synthesized from ethanol using it. As the second catalyst, for example, a catalyst including an oxide of a metal belonging to Group 4 to Group 13 in the periodic table and magnesium oxide. In the second catalyst, it is preferable that the metal belonging to Group 4 to Group 13 in the periodic table be bonded to magnesium oxide through one or more selected from magnesia and silica.

Preferable examples of the second catalyst include a catalyst in which tantalum oxide is bonded through magnesia and silica ($Ta_2O_5/MgO/SiO_2$ (mass ratio=2/83/15), refer to PCT International Publication No. WO2013/125389).

The second catalyst is produced using a well-known method.

Examples of a method of producing the second catalyst include a method including: dispersing a sol of a catalyst metal in a sol of one or more selected from magnesia and silica to obtain a catalyst sol; and firing the catalyst sol.

It is preferable that the pipe 46 and the pipe 47 be formed of a material which is inert with butadiene and, for example, be formed of a stainless steel pipe.

In the embodiment, the pipe 46 includes a pressure control portion 30. The pressure control portion 30 is not particularly limited as long as it can adjust the internal pressure of the reaction pipe 24 to an arbitrary value. For example, a well-known pressure valve is used.

As the gas-liquid separator 26, a well-known gas-liquid separator formed of a material which is inert with butadiene, hydrogen, and the like can be adopted.

In the gas-liquid separator 26, butadiene is separated by liquefying butadiene in a state where hydrogen, which is produced as a by-product, is gaseous. The separated and purified butadiene is collected in a storage tank or the like (not shown) through the pipe 47.

The return means 18 is means for returning hydrogen, which is produced as a by-product in the butadiene production device 16, to the ethanol production device 12. The return means 18 includes a pipe through which the gas-liquid separator 26 of the butadiene production device 16 and the ethanol production device 12 are connected.

It is preferable that the pipe of the return means 18 be formed of a material which is inert with hydrogen and, for example, be formed of a stainless steel pipe.

Optionally, a valve, a pump, a separation membrane, or the like is connected to the pipe of the return means 18.

A position of the ethanol production device 12 to which the pipe of the return means 18 is connected is not particularly limited as long as the returned hydrogen is in a range where it is not sufficiently consumed in the reactor bed 12a. For example, the pipe of the return means 18 may be connected to a portion of the ethanol production device 12 close to a gas supply port (close to the reforming furnace 22), to the center of the ethanol production device 12, or to a portion of the ethanol production device 12 close to a gas exhaust port (close to the purification device 14).

In the butadiene production system 1, the solid raw materials are thermally decomposed in the gasification furnace 20 of the gas preparation device 10 to produce the mixed gas including hydrogen and carbon monoxide. The mixed gas is supplied to the reforming furnace 22 through the pipe 41, and hydrocarbon in the mixed gas reacts with water in the reforming furnace 22 to be reformed into a mixed gas having a higher carbon monoxide concentration.

The reformed mixed gas is supplied from the reforming furnace 22 to the ethanol production device 12 through the pipe 42 and brought into contact with the first catalyst to react with the first catalyst such that a gaseous primary product including ethanol and acetaldehyde is obtained. The primary product is supplied to the purification device 14 through the pipe 43 and is purified. The reformed primary product is supplied to the reaction pipe 24 of the butadiene production device 16 through the pipe 45.

Ethanol in the gaseous primary product supplied to the reaction pipe 24 is brought into contact with the second catalyst to react with the second catalyst such that a gaseous secondary product including butadiene and hydrogen is obtained. The secondary product is supplied to the gas-liquid separator 26 through the pipe 46, and the liquid butadiene and the gaseous by-products including hydrogen are separated from each other. Butadiene is collected through the pipe 47.

Hydrogen, which is produced as a by-product, is returned to the ethanol production device 12 by the return means 18.

(Butadiene Production Method)

Hereinafter, a method of producing the butadiene production system 1 will be described as an example of a butadiene production method according to the present invention. The butadiene production method according to the embodiment includes a gas preparation step, an ethanol production step, a butadiene production step, and a return step described below.

Gas preparation step: a step of heating raw materials to prepare a mixed gas including hydrogen and carbon monoxide Ethanol production step: a step of bringing the mixed gas into contact with a first catalyst to obtain ethanol Butadiene production step: a step of bringing the ethanol into contact with a second catalyst to obtain butadiene Return step: a step returning hydrogen, which is produced as a by-product in the butadiene production step, to the gas preparation step <Gas Preparation Step>

The gas preparation step according to the embodiment includes a gasification operation and a reforming operation, in the gasification operation, solid raw materials are thermally decomposed to produce the mixed gas including hydrogen and carbon monoxide, and in the reforming operation, hydrocarbon in the mixed gas is reformed into hydrogen and carbon monoxide by causing it to react with water.

In the gasification operation, in the gasification furnace 20 of the gas preparation device 10, a portion of the crushed solid raw materials such as biomass, organic waste (for example, waste plastic, waste paper, or waste cloth), or coal is fired in the presence of oxygen. As a result, the solid raw materials are thermally decomposed and gasified to produce the mixed gas including hydrogen and carbon monoxide.

A temperature for the thermal decomposition of the solid raw materials in the gasification operation is not particularly limited as long as it is a temperature at which the mixed gas including hydrogen and carbon monoxide is produced. The temperature for the thermal decomposition is preferably 200° C. to 1000° C. and more preferably 500° C. to 800° C. In a case where the temperature for the thermal decomposition is lower than the lower limit value, substantially no solid raw materials are gasified, and the object cannot be achieved. In a case where the temperature for the thermal decomposition is higher than the upper limit value, the proportion of the solid raw materials to be fired to increase the temperature increases, and the proportions of hydrogen and carbon monoxide in the mixed gas decrease.

In the reforming operation, in the reforming furnace 22, hydrocarbon in the mixed gas which is supplied from the gasification furnace 20 through the pipe 41 is caused to react with water. As a result, hydrocarbon is reformed into hydrogen and carbon monoxide, the concentration of carbon monoxide is increased, and thus a mixed gas having a desired ratio between hydrogen and carbon monoxide is obtained.

A temperature for heating the mixed gas in the reforming operation is higher than the temperature for the thermal decomposition in the gasification operation and is preferably 800° C. to 2000° C. and more preferably 1000° C. to 1500° C. In a case where the heating temperature is lower than the lower limit value, the reaction does not proceed sufficiently, and the concentration of carbon monoxide is not increased. In a case where the heating temperature is higher than the upper limit value, high heat-resistance is required for the material of the reforming furnace, and thus environmental load is increased.

The total proportion of hydrogen and carbon monoxide in the mixed gas prepared in the gas preparation step is preferably 50 vol % or higher, more preferably 80 vol % or higher, and still more preferably 90 vol % or higher. As the total proportion of hydrogen and carbon monoxide increases, the yield of ethanol can be easily increased. The upper limit value of the total proportion of hydrogen and carbon monoxide in the mixed gas prepared in the gas preparation step is 100 vol %.

The mixed gas may include not only hydrogen and carbon monoxide but also methane, ethane, ethylene, nitrogen, carbon dioxide, water, and the like.

<Ethanol Production Step>

The mixed gas is supplied from the reforming furnace 22 of the gas preparation device 10 to the ethanol production device 12 through the pipe 42. The mixed gas supplied to the ethanol production device 12 is brought into contact with the first catalyst such that the primary product including ethanol and acetaldehyde is obtained.

In the embodiment, in a case where the metal catalyst is used as the first catalyst, the primary product is gaseous.

The total proportion of hydrogen and carbon monoxide is preferably 50 vol % or higher, more preferably 80 vol % or higher, and still more preferably 90 vol % or higher with respect to the total volume of the mixed gas supplied from the gas preparation step and hydrogen returned by the return step. As the total proportion of hydrogen and carbon monoxide increases, the yield of ethanol can be easily increased. The upper limit value of the total proportion of hydrogen and carbon monoxide is 100 vol %.

A ratio $H_2/CO$ between hydrogen and carbon monoxide supplied to the ethanol production step is preferably 1/2 to 4/1, more preferably 1/1 to 3/1, and still more preferably 1.5/1 to 2.5/1. In a case where the ratio $H_2/CO$ is in the above-described range, the synthesis efficiency of ethanol can be easily increased.

The temperature (reaction temperature) at which the mixed gas is brought into contact with the first catalyst, that is, the temperature of the reactor bed 12a is preferably 150° C. to 450° C., more preferably 200° C. to 400° C., and still more preferably 250° C. to 350° C. In a case where the reaction temperature is the lower limit value or higher, the catalyst reaction speed is sufficiently increased, and ethanol can be produced more efficiently. In a case where the reaction temperature is the upper limit value or lower, the selection ratio of ethanol can be increased.

The pressure (reaction pressure) at which the mixed gas is brought into contact with the first catalyst, that is, the internal pressure of the ethanol production device 12A is preferably 0.5 to 10 MPa, more preferably 1 to 7.5 MPa, and still more preferably 2 to 5 MPa. In a case where the reaction pressure is the lower limit value or higher, the catalyst reaction speed is sufficiently increased, and ethanol can be produced more efficiently. In a case where the reaction pressure is the upper limit value or lower, the selection ratio of ethanol can be increased.

A space velocity of the gas in the reactor bed 12a (a value obtained by dividing the supply amount of gas per unit time by the amount of the catalyst (in terms of volume)) in terms of values measured under standard conditions is preferably 10 to 100000 L/L-catalyst/hr, more preferably 1000 to 50000 L/L-catalyst/hr, and still more preferably 3000 to 20000 L/L-catalyst/hr. The space velocity is appropriately adjusted in consideration of the reaction pressure, the reaction temperature, and the composition of the mixed gas as a raw material.

In a case where the primary product according to the embodiment includes acetaldehyde, a molar ratio represented by ethanol/acetaldehyde (hereinafter, also referred to as "ratio EtOH/AcH") is preferably 1/5 to 5/1. In a case where the ratio EtOH/AcH is in the above-described range, the yield of butadiene can be further increased.

The ratio EtOH/AcH in the primary product can be easily adjusted by combining the composition of the metal catalyst as the first catalyst, the average pore diameter of the support of the metal catalyst, the reaction temperature, the reaction pressure, and the like. For example, in a case where the reaction temperature is increased, the selection ratio of ethanol is increased, and the ratio EtOH/AcH is increased.

The primary product including ethanol obtained in the ethanol production device 12 is supplied to the purification device 14 through the pipe 43 and is purified to remove materials other than ethanol and acetaldehyde. Next, the purified primary product is supplied to the butadiene production device 16 through the pipe 45.

<Butadiene Production Step>

The primary product including ethanol is supplied to the reaction pipe 24 of the butadiene production device 16 and is brought into contact with the second catalyst of the reactor bed 24a. As a result, the secondary product including butadiene and hydrogen is obtained due to the reaction represented by the following formula (6). The obtained secondary product is gaseous.

$$2C_2H_5OH \rightarrow C_4H_6 + H_2 + 2H_2O \qquad (6)$$

By using the second catalyst, butadiene can be synthesized from ethanol and acetaldehyde.

The temperature (reaction temperature) at which the primary product is brought into contact with the second catalyst, that is, the temperature of the reactor bed 24a is preferably 300° C. to 500° C. and more preferably 350° C. to 450° C. In a case where the reaction temperature is the lower limit value or higher, the catalyst reaction speed is sufficiently increased, and butadiene can be produced more efficiently. In a case where the reaction temperature is the upper limit value or lower, deterioration in the second catalyst is likely to be inhibited.

The pressure (reaction pressure) at which the primary product is brought into contact with the second catalyst, that is, the internal pressure of the reaction pipe 24 is, for example, normal pressure to 1 MPa.

The proportion of ethanol in the primary product supplied in the butadiene production step is preferably 70 mass % or higher and more preferably 90 mass % or higher. In a case where the proportion of ethanol is the lower limit value or higher, the synthesis efficiency of butadiene can be further increased.

A space velocity of the primary product in the reactor bed 24a in terms of values measured under standard conditions is preferably 100 to 50000 L/L-catalyst/hr, more preferably 200 to 10000 L/L-catalyst/hr, and still more preferably 300 to 5000 L/L-catalyst/hr. The space velocity is appropriately adjusted in consideration of the reaction pressure, the reaction temperature, and the composition of the primary product.

Next, the secondary product is supplied from the reaction pipe 24 to the gas-liquid separator 26 through the pipe 46, the temperature is decreased, and the liquid butadiene and the gaseous hydrogen, which is produced as a by-product, are separated from each other. Butadiene is collected in a storage tank or the like (not shown) through the pipe 47.

<Return Step>

Hydrogen, which is produced as a by-product in the butadiene production step, is returned to the ethanol production step. Specifically, hydrogen, which is separated from butadiene in the gas-liquid separator 26, is returned to the ethanol production device 12 by the return means 18. Optionally, the returned hydrogen is separated from by-products other than hydrogen by a separation membrane or the like.

By returning hydrogen to the ethanol production step, a ratio between carbon monoxide and hydrogen can be easily adjusted to be suitable for the ethanol production reaction using the first catalyst. Therefore, the synthesis efficiency of ethanol is increased. As a result, the final yield of butadiene is increased.

Regarding the amount of hydrogen returned, the ratio $H_2/CO$ between hydrogen and carbon monoxide after hydrogen is brought into contact with the mixed gas supplied from the gas preparation step is preferably 1/2 to 4/1 and more preferably 1/1 to 3/1. In a case where the amount of hydrogen returned is the lower limit value or higher, butadiene can be easily produced with a high yield. In a case where the amount of hydrogen returned is the upper limit value or lower, the adjustment of the ratio $H_2/CO$ is easily performed.

For example, in a case where ethanol is obtained from hydrogen and carbon monoxide using the metal catalyst, the reaction efficiency is the highest at a $H_2/CO$ ratio of 2/1. However, the ratio $H_2/CO$ in the mixed gas, which is obtained by firing raw materials such as organic waste and reforming the fired raw materials, is typically about 1/1. Therefore, the amount of hydrogen in the ethanol production step is likely to be insufficient. By adding, for example, a step of performing a shift reaction ($CO+H_2O \rightarrow CO_2+H_2$) using a catalyst such as iron oxide ($Fe_3O_4$) or platinum, the ratio $H_2/CO$ can also be increased. In this case, however, there is a problem in that the production amount of ethanol is relatively small. In addition, in a case where such a step is added, the production steps become complicated.

On the other hand, in the butadiene production method according to the embodiment, hydrogen, which is produced as a by-product in the butadiene production step, is returned. As a result, although hydrogen is not newly added, the proportion of hydrogen in the ethanol production step can be easily increased. Therefore, the ratio $H_2/CO$ can be easily adjusted to be suitable for the ethanol production reaction using the first catalyst. Therefore, ethanol can be efficiently obtained, and thus the final yield of butadiene is increased.

The gas preparation device included in the butadiene production system according to the first embodiment is not particularly limited as long as it can heat the raw materials to produce the mixed gas including hydrogen and carbon monoxide. For example, the gas preparation device may include only the reforming furnace without including the gasification furnace, in which raw material gases such as natural gas or waste gas emitted from a factory are reformed in the reforming furnace so as to prepare the mixed gas including hydrogen and carbon monoxide. The gas preparation device may include a gasification-reforming furnace including both functions of the gasification furnace and the reforming furnace.

The return means included in the butadiene production system according to the first embodiment may be means for storing hydrogen or by-products including hydrogen obtained from the butadiene production device in a storage tank or the like and returning the stored hydrogen or by-products to the ethanol production device using various kinds of transport means such as transport using a vehicle. However, from the viewpoint of reducing energy loss, it is preferable that the return means be return means using a pipe.

The butadiene production method according to the first embodiment is not limited to the method using the above-described butadiene production system 1.

In the butadiene production method according to the first embodiment, the gas preparation step may include only the reforming operation without including the gasification operation. In the gas preparation step, the gasification operation and the reforming operation may be performed at the same time.

Second Embodiment

Hereinafter, a second embodiment of the butadiene production system and the butadiene production method according to the present invention will be described. In a butadiene production system and the butadiene production method according to the embodiment, the raw materials are heated to prepare the mixed gas including hydrogen and carbon dioxide, ethanol is obtained from the mixed gas using a third catalyst, and butadiene is produced from the ethanol.

(Butadiene Production System)

Figure 2:
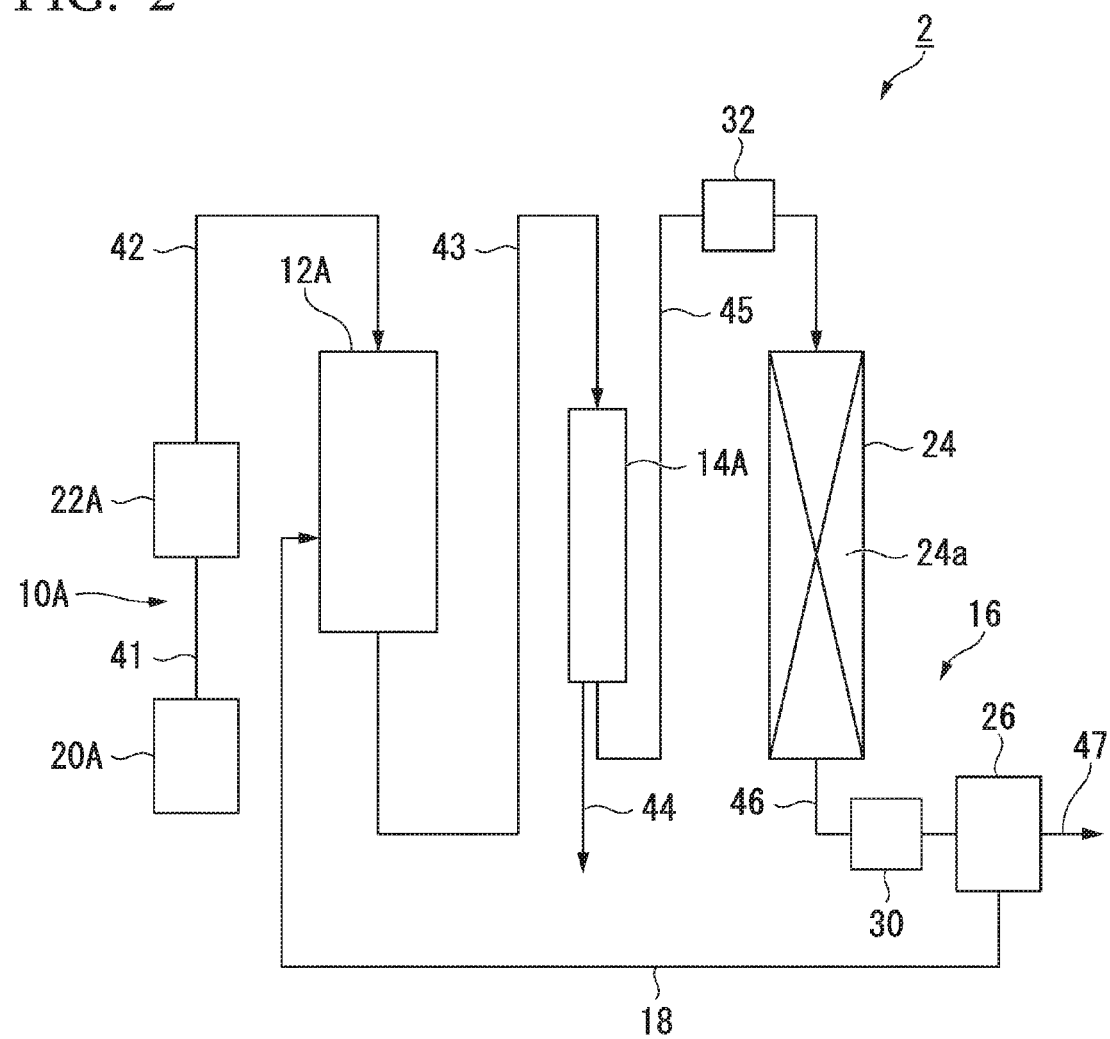
FIG. 2 is a schematic diagram showing another example of the butadiene production system according to the present invention.

FIG. 2 is a schematic diagram showing a butadiene production system 2 according to the embodiment. In FIG. 2, the same components as those in FIG. 1 will be represented by the same reference numerals, and the description thereof will not be repeated.

The butadiene production system 2 includes: a gas preparation device 10A; an ethanol production device 12A that is provided downstream of the gas preparation device 10A; a purification device 14A that is provided downstream of the ethanol production device 12A; a butadiene production device 16 that is provided downstream of the purification device 14A; and the return means 18 for returning hydrogen from the butadiene production device 16 to the ethanol production device 12A. The gas preparation device 10A includes a gasification furnace 20A and a reforming furnace 22A that is provided downstream of the gasification furnace 20A.

The gasification furnace 20A and the reforming furnace 22A are connected to each other through the pipe 41. The reforming furnace 22A and the ethanol production device 12A are connected to each other through the pipe 42. The ethanol production device 12A and the purification device 14A are connected to each other through the pipe 43. The exhaust pipe 44 is connected to the purification device 14A. The purification device 14A and the reaction pipe 24 of the butadiene production device 16 are connected to each other through the pipe 45.

The gas preparation device 10A heats raw materials to prepare a mixed gas including hydrogen and carbon dioxide at an arbitrary ratio, and includes the gasification furnace 20A and the reforming furnace 22A.

The gasification furnace 20A thermally decomposes solid raw materials such as biomass, organic waste (for example, waste plastic, waste paper, or waste cloth), or coal to produce a mixed gas including hydrogen and carbon dioxide. Examples of the gasification furnace 20A are the same as described above regarding the gasification furnace 20 according to the first embodiment. The mixed gas obtained in the gasification furnace 20A includes carbon monoxide.

In the reforming furnace 22A, the mixed gas obtained in the gasification furnace 20A is reformed into a gas in which the concentration of carbon dioxide and the concentration of hydrogen are high. Examples of the reforming furnace 22A include a furnace for performing a shift reaction ($CO + H_2O \rightarrow CO_2 + H_2$) using a catalyst such as iron oxide ($Fe_3O_4$) or platinum.

In the embodiment, in the pipe 42, a gas disperser which saturates liquid such as water with the mixed gas by aeration or the like may be provided such that the liquid saturated with the mixed gas is supplied to the ethanol production device 12A.

The ethanol production device 12A brings the mixed gas, which has been supplied from the gas preparation device 10A, into contact with the third catalyst to obtain ethanol. As the third catalyst according to the embodiment, a catalyst for synthesizing ethanol from hydrogen and carbon dioxide can be adopted, and a microorganism ($CO_2$-assimilating bacterium) capable of ethanol fermentation in which carbon dioxide is used as a substrate.

In the ethanol production device 12A, by bringing the mixed gas into contact with the third catalyst, a primary product including ethanol is obtained.

The ethanol production device 12A is not particularly limited as long as it can produce ethanol by ethanol fermentation using a microorganism. For example, a well-known bioreactor can be adopted. Examples of the bioreactor include a continuously stirred tank reactor, an immobilized cell reactor, a trickle bed reactor, a bubble column, a gas lift fermenter, a membrane reactor (for example, a hollow fiber membrane reactor), and a static mixer.

As a material of the ethanol production device 12A, a material which is inert with the mixed gas and ethanol is preferable.

As the $CO_2$-assimilating bacterium, a well-known microorganism capable of ethanol fermentation in which carbon dioxide is used as a substrate can be adopted. As the $CO_2$-assimilating bacterium, for example, genus *Moorella* can be used.

As the third catalyst, one kind may be used alone, or two or more kinds may be used.

In the embodiment, in the pipe 43, a pressure control portion which controls the internal pressure of the ethanol production device 12A may be provided. By the pressure control portion increasing the internal pressure of the ethanol production device 12A to be higher than the atmospheric pressure, the mixed gas and the returned hydrogen are easily dissolved in the reaction solution, and the yield of ethanol is further increased.

The purification device 14A removes materials (for example, by-products, water, unreacted mixed gas, a culture medium, or a catalyst) other than ethanol from the primary product. Examples of the purification device 14A include a distillation device, a gas-liquid separator, a solid-liquid separator, and a combination thereof.

The materials removed by the purification device 14A are exhausted through the exhaust pipe 44. It is preferable that the exhaust pipe 44 be formed of a material which is inert with the materials removed by the purification device 14A and, for example, be formed of a stainless steel pipe.

In the pipe 45, a heating device 32 which heats liquid ethanol to be gasified is provided. As a result, ethanol in the gasified state is supplied to the butadiene production device 16.

The heating device 32 is not particularly limited as long as it heats ethanol to be gasified. For example, a well-known heating device can be adopted. As a material of the heating device 32, a material which is inert with ethanol is preferable.

The return means 18 according to the embodiment may supply the returned hydrogen into a reaction solution in the ethanol production device 12A, or may supply the returned hydrogen into a gas phase in the ethanol production device 12A. In the pipe of the return means 18, a gas disperser which saturates liquid such as water with the returned hydrogen by aeration or the like may be provided such that the liquid saturated with hydrogen is supplied to the ethanol production device 12A.

In the butadiene production system 2, the solid raw materials are thermally decomposed in the gasification furnace 20A of the gas preparation device 10A to produce the mixed gas including hydrogen and carbon dioxide. The mixed gas is supplied to the reforming furnace 22A through the pipe 41 and is reformed into a mixed gas in which the concentration of carbon dioxide and the concentration of hydrogen are high.

The mixed gas is supplied from the reforming furnace 22A to the ethanol production device 12A through the pipe 42 and brought into contact with the third catalyst to react with the third catalyst such that a liquid primary product including ethanol is obtained. The primary product is supplied to the purification device 14A through the pipe 43 and is purified. The purified primary product which is gasified by the heating device 32 is supplied to the reaction pipe 24 of the butadiene production device 16 through the pipe 45.

Ethanol in the gaseous primary product supplied to the reaction pipe 24 is brought into contact with the second catalyst to react with the second catalyst such that a gaseous secondary product including butadiene and hydrogen is obtained. The secondary product is supplied to the gas-liquid separator 26 through the pipe 46, and the liquid butadiene and the gaseous hydrogen are separated from each other. Butadiene is collected through the pipe 47.

Hydrogen, which is produced as a by-product, is returned to the ethanol production device 12A by the return means 18.

(Butadiene Production Method)

Hereinafter, a butadiene production method using the above-described butadiene production system 2 will be described. The butadiene production method according to the embodiment includes a gas preparation step, an ethanol production step, a butadiene production step, and a return step described below.

Gas preparation step: a step of heating raw materials to prepare a mixed gas including hydrogen and carbon dioxide Ethanol production step: a step of bringing the mixed gas into contact with a third catalyst to obtain ethanol Butadiene production step: a step of bringing the ethanol into contact with a second catalyst to obtain butadiene Return step: a step returning hydrogen, which is produced as a by-product in the butadiene production step, to the gas preparation step <Gas Preparation Step>

The gas preparation step according to the embodiment includes a gasification operation and a reforming operation, in the gasification operation, solid raw materials are thermally decomposed to produce the mixed gas including hydrogen and carbon dioxide, and in reforming operation, the mixed gas is reformed into a gas in which the concentration of carbon dioxide and the concentration of hydrogen are high.

In the gasification operation, in the gasification furnace 20A of the gas preparation device 10A, a portion of the solid raw materials is fired in the presence of oxygen. As a result, the solid raw materials are thermally decomposed and gasified to produce the mixed gas including hydrogen and carbon dioxide.

In the reforming operation, in the reforming furnace 22A, the mixed gas supplied from the gasification furnace 20A through the pipe 41 undergoes the shift reaction and thus is reformed into a mixed gas in which the concentration of carbon dioxide and the concentration of hydrogen are high.

A ratio $H_2/CO_2$ in the mixed gas prepared in the gas preparation step according to the embodiment is preferably 1/2 to 5/1, more preferably 1/1 to 4/1, and still more preferably 1.5/1 to 3/1. In a case where the ratio $H_2/CO_2$ is in the above-described range, the yield of ethanol can be easily increased.

<Ethanol Production Step>

The mixed gas whose temperature is decreased is supplied from the reforming furnace 22A of the gas preparation device 10A to the ethanol production device 12A through the pipe 42. In the ethanol production device 12A, the $CO_2$-assimilating bacterium as the third catalyst is present in a reaction solution including water, a culture medium, and the like, and an environment is adjusted so as to be capable of ethanol fermentation in which the microorganism is used. The mixed gas supplied to the ethanol production device 12A is brought into contact with the CO2-assimilating bacterium such that the primary product including ethanol is obtained by ethanol fermentation.

In the embodiment, the primary product is a mixture of liquid (for example, ethanol or water) and gas (for example, unreacted mixed gas).

The total proportion of hydrogen and carbon dioxide is preferably 50 vol % or higher, more preferably 80 vol % or higher, and still more preferably 90 vol % or higher with respect to the total volume of the mixed gas supplied from the gas preparation step and hydrogen returned by the return step. As the total proportion of hydrogen and carbon dioxide increases, the yield of ethanol can be easily increased. The upper limit value of the total proportion of hydrogen and carbon dioxide is 100 vol %.

A ratio $H_2/CO_2$ between hydrogen and carbon dioxide supplied to the ethanol production step is preferably 1/2 to 5/1, more preferably 1/1 to 4/1, and still more preferably 1.5/1 to 3/1. In a case where the ratio $H_2/CO_2$ is in the above-described range, the yield of ethanol can be easily increased.

The temperature of the mixed gas supplied to the ethanol production device 12A is preferably decreased to 30° C. to 70° C. and is more preferably decreased to 50° C. to 60° C. In a case where the temperature of the mixed gas supplied is in the above-described range, a decrease in the amount of the microorganism caused by heat is easily inhibited.

It is preferable that the supply amount of the mixed gas to the ethanol production device 12A be adjusted such that hydrogen and carbon dioxide are saturated in the liquid such as water. In a case where the supply amount of the mixed gas is in the above-described range, ethanol can be produced more efficiently.

A reaction temperature in the ethanol production device 12A is preferably 50° C. to 65° C. and more preferably 55° C. to 60° C. In a case where the reaction temperature is in the above-described range, ethanol can be produced more efficiently.

An internal pressure (reaction pressure) of the ethanol production device 12A is preferably 0 to 1 MPa, more preferably 0.2 to 0.8 MPa, and still more preferably 0.4 to 0.6 MPa. In a case where the reaction pressure is the lower limit value or higher, hydrogen and carbon dioxide in the mixed gas are likely to be dissolved in the reaction solution, and ethanol can be produced more efficiently. In a case where the reaction pressure is higher than the upper limit value, high-pressure resistance is required, and thus environmental load is increased.

The primary product including ethanol obtained in the ethanol production device 12A is supplied to the purification device 14A through the pipe 43 and is purified by distillation, gas-liquid separation, and the like to remove materials other than ethanol. Next, the purified primary product which is heated to be gasified by the heating device 32 is supplied to the butadiene production device 16 through the pipe 45.

<Butadiene Production Step>

The butadiene production step according to the embodiment is performed using the same method as in the butadiene production system 1.

<Return Step>

Hydrogen, which is produced as a by-product in the butadiene production step, is returned to the ethanol production step. Specifically, hydrogen, which is separated from butadiene in the gas-liquid separator 26, is returned to the ethanol production device 12A by the return means 18. Optionally, the returned hydrogen is separated from by-products other than hydrogen by a separation membrane or the like.

Hydrogen returned by the return means 18 may be supplied to a reaction solution or a gas phase in the ethanol production device 12A.

Regarding the amount of hydrogen returned, the ratio $H_2/CO_2$ between hydrogen and carbon dioxide after hydrogen is brought into contact with the mixed gas supplied from the gas preparation step is preferably 1/2 to 5/1 and more preferably 1/1 to 4/1. In a case where the amount of hydrogen returned is the lower limit value or higher, butadiene can be easily produced with a high yield. In a case where the amount of hydrogen returned is the upper limit value or lower, the adjustment of the ratio $H_2/CO_2$ is easily performed.

In the embodiment, in a case where the proportion of hydrogen is higher than that of carbon dioxide, the synthesis efficiency of ethanol is high.

In the butadiene production method according to the embodiment, as in the case of the first embodiment, hydrogen, which is produced as a by-product in the butadiene production step, is returned. As a result, the proportion of hydrogen in the ethanol production step can be easily increased. Therefore, as compared to a case where hydrogen is not returned, ethanol can be produced more efficiently, and thus butadiene can be obtained with a high yield.

The butadiene production system according to the second embodiment is not limited to the above-described butadiene production system 2.

For example, in the butadiene production system according to the second embodiment, hydrogen may be returned from the gas-liquid separator of the butadiene production device to a pipe provided upstream of the ethanol production device.

The gas preparation device included in the butadiene production system according to the second embodiment is not particularly limited as long as it can heat the raw materials to produce the mixed gas including hydrogen and carbon dioxide. For example, the gas preparation device may include only the gasification furnace without including the reforming furnace. In addition, the gas preparation device may include only the reforming furnace without including the gasification furnace, in which raw material gases such as natural gas or waste gas emitted from a factory are heated and reformed in the reforming furnace so as to prepare the mixed gas including hydrogen and carbon dioxide. The gas preparation device may include a gasification-reforming furnace including both functions of the gasification furnace and the reforming furnace.

The return means included in the butadiene production system according to the second embodiment may be means for storing hydrogen or by-products including hydrogen obtained from the butadiene production device in a storage tank or the like and returning the stored hydrogen or by-products to the ethanol production device using various kinds of transport means such as transport using a vehicle. However, from the viewpoint of reducing energy loss, it is preferable that the return means be return means using a pipe.

The butadiene production method according to the second embodiment is not limited to the method using the above-described butadiene production system 2.

In the butadiene production method according to the present invention, the gas preparation step may include only the gasification operation without including the reforming operation, or may include only the reforming operation without including the gasification operation. In the gas preparation step, the gasification operation and the reforming operation may be performed at the same time.

Hereinafter, the present invention will be described in detail using Examples. However, the present invention is not limited to the following description.

[Component Analysis]

The amounts of butadiene, hydrogen, and ethylene in a secondary product obtained in each example were measured by gas chromatography.

Example 1

Butadiene was produced using the butadiene production system 1 shown in FIG. 1.

Specifically, 400 g/hr of a simulated waste simulating an industrial waste (combustible content: 76%, ash content: 9%, water content: 15%, amount of heat: 4000 kcal/kg) was gasified in the gasification furnace 20, and a water vapor reforming reaction was performed in the reforming furnace 22. As a result, a mixed gas was obtained. Next, 3 g/hr of hydrogen returned from the butadiene production device 16 was further mixed with the mixed gas, and 650 NL/hr of the mixed gas was supplied to the ethanol production device 12.

In the ethanol production device 12, 158 g/hr of ethanol was obtained due to a reaction using a rhodium catalyst. In the ethanol production device 12, the reaction temperature was 280° C., and the reaction pressure was 2 MPa.

The primary product including ethanol obtained in the ethanol production device 12 was purified by a distiller as the purification device 14 and was supplied to the butadiene production device 16. As a result, the secondary product including butadiene was obtained. As the second catalyst, a tantalum catalyst was used. In the reaction pipe 24, the reaction temperature was 420° C. and the reaction pressure was 0.1 MPa, and the supply amount of the mixed gas was 158 g/hr.

Finally, 93 g/hr of butadiene and 3 g/hr of hydrogen were obtained in the butadiene production device 16. The yield of butadiene was 88%.

Comparative Example 1

Butadiene was produced using the same method as in Example 1, except that hydrogen which was produced as a by-product in the butadiene production device 16 was not returned to the ethanol production device 12. In the reforming furnace 22, 615 NL/hr of a mixed gas was obtained. In the ethanol production device 12, 145 g/hr of ethanol was obtained.

Finally, 85 g/hr of butadiene and 3 g/hr of hydrogen were obtained in the butadiene production device 16. The yield of butadiene was 82%.

REFERENCE SIGNS LIST

1,2: BUTADIENE PRODUCTION SYSTEM
10, 10A: GAS PREPARATION DEVICE
12, 12A: ETHANOL PRODUCTION DEVICE
14, 14A: PURIFICATION DEVICE
16: BUTADIENE PRODUCTION DEVICE
18: RETURN MEANS
20, 20A: GASIFICATION FURNACE
22, 22A: REFORMING FURNACE
24: REACTION PIPE
26: GAS-LIQUID SEPARATOR
41 to 43, 45 to 47: PIPE
44: EXHAUST PIPE

The invention claimed is:

1. A butadiene production system, comprising:
    a gas preparation device that heats raw materials to prepare a mixed gas comprising hydrogen and carbon monoxide;
    an ethanol production device that is provided downstream of the gas preparation device and brings the mixed gas into contact with a catalyst (X) to obtain ethanol;
    a butadiene production device that is provided downstream of the ethanol production device and brings the ethanol into contact with a catalyst (Y) different from the catalyst (X) to obtain butadiene; and
    a return means for returning hydrogen, which is produced as a by-product in the butadiene production device, to the ethanol production device.

2. A butadiene production system, comprising:
    a gas preparation device that heats raw materials to prepare a mixed gas comprising hydrogen and carbon dioxide;
    an ethanol production device that is provided downstream of the gas preparation device and brings the mixed gas into contact with a catalyst (Z) to obtain ethanol;
    a butadiene production device that is provided downstream of the ethanol production device and brings the ethanol into contact with a catalyst (Y) different from the catalyst (Z) to obtain butadiene; and a return means for returning hydrogen, which is produced as a by-product in the butadiene production device, to the ethanol production device.

3. The butadiene production system according to claim 1, wherein the return means comprises a pipe through which the butadiene production device and the ethanol production device are connected.

4. A method of producing butadiene, comprising:

a gas preparation step of heating raw materials to prepare a mixed gas comprising hydrogen and carbon monoxide;

an ethanol production step of bringing the mixed gas into contact with a catalyst (X) to obtain ethanol;

a butadiene production step of bringing the ethanol into contact with a catalyst (Y) different from the catalyst (X) to obtain butadiene; and a return step of returning hydrogen, which is produced as a by-product in the butadiene production step, to the ethanol production step.

5. A method of producing butadiene, comprising:

a gas preparation step of heating raw materials to prepare a mixed gas comprising hydrogen and carbon dioxide;

an ethanol production step of bringing the mixed gas into contact with a catalyst (Z) to obtain ethanol;

a butadiene production step of bringing the ethanol into contact with a catalyst (Y) different from the catalyst (Z) to obtain butadiene; and a return step of returning hydrogen, which is produced as a by-product in the butadiene production step, to the ethanol production step.

6. The butadiene production system according to claim 2, wherein the return means comprises a pipe through which the butadiene production device and the ethanol production device are connected.

7. The butadiene production system according to claim 1, wherein the catalyst (X) is a hydrogenation-active metal or an aggregate of a hydrogenation-active metal and an auxiliary active metal, wherein the hydrogenation-active metal is at least one metal selected from the group consisting of an alkali metal, an element belonging to Group 7 of the periodic table, an element belonging to Group 8 of the periodic table, an element belonging to Group 9 of the periodic table, and an element belonging to Group 10 of the periodic table, and the catalyst (Y) is a catalyst comprising an oxide of a metal belonging to Group 4 through Group 13 of the periodic table and magnesium oxide.

8. The butadiene production system according to claim 2, wherein the catalyst (Z) is a $CO_2$-assimilating bacterium, and the catalyst (Y) is a catalyst comprising an oxide of a metal belonging to Group 4 through Group 13 of the periodic table and magnesium oxide.

9. The butadiene production method according to claim 4, wherein the catalyst (X) is a hydrogenation-active metal or an aggregate of a hydrogenation-active metal and an auxiliary active metal, wherein the hydrogenation-active metal is at least one metal selected from the group consisting of an alkali metal, an element belonging to Group 7 of the periodic table, an element belonging to Group 8 of the periodic table, an element belonging to Group 9 of the periodic table, and an element belonging to Group 10 of the periodic table, and the catalyst (Y) is a catalyst comprising an oxide of a metal belonging to Group 4 through Group 13 of the periodic table and magnesium oxide.

10. The butadiene production method according to claim 5, wherein the catalyst (Z) is a $CO_2$-assimilating bacterium, and the catalyst (Y) is a catalyst comprising an oxide of a metal belonging to Group 4 through Group 13 of the periodic table and magnesium oxide.

* * * * *